(12) United States Patent
Stave et al.

(10) Patent No.: US 7,532,321 B2
(45) Date of Patent: May 12, 2009

(54) COMPOSITIONS AND METHODS FOR THE DETECTION OF WATER TREATMENT POLYMERS

(75) Inventors: James W. Stave, Bear, DE (US); Matthew H. Knight, West Chester, PA (US)

(73) Assignee: Strategic Diagnostics Inc., Newark, DE (US)

( * ) Notice: Subject to any disclaimer, the term of this patent is extended or adjusted under 35 U.S.C. 154(b) by 78 days.

(21) Appl. No.: 11/852,825

(22) Filed: Sep. 10, 2007

(65) Prior Publication Data

US 2008/0062417 A1    Mar. 13, 2008

Related U.S. Application Data

(60) Provisional application No. 60/843,031, filed on Sep. 8, 2006.

(51) Int. Cl.
*G01J 3/44* (2006.01)
*G01N 21/65* (2006.01)

(52) U.S. Cl. ..................................... 356/301
(58) Field of Classification Search ................ 356/301
See application file for complete search history.

(56) References Cited

U.S. PATENT DOCUMENTS

| | | |
|---|---|---|
| 6,585,933 B1 | 7/2003 | Ehrhardt et al. |
| 6,750,328 B1 | 6/2004 | Wetegrove et al. |
| 2001/0016182 A1 | 8/2001 | Cronin et al. |
| 2003/0142301 A1 | 7/2003 | Coleman et al. |

FOREIGN PATENT DOCUMENTS

| | | |
|---|---|---|
| WO | WO2004008090 | 1/2004 |
| WO | WO2004105595 | 12/2004 |
| WO | WO2005038437 | 4/2005 |

OTHER PUBLICATIONS

PCT Search Report dated Dec. 20, 2007 for PCT/US2007/078047.

*Primary Examiner*—F. L Evans
(74) *Attorney, Agent, or Firm*—Kilpatrick Stockton LLP

(57) ABSTRACT

Compositions and methods utilizing Raman Spectroscopy to detect and determine, directly or indirectly, the concentration of water treatment polymers in water or methods for measuring or quantifying the amount of water treatment polymer in a sample, such as an industrial, commercial, or municipal water sample, are provided. The compositions contain water treatment polymers that have been modified to include one or more Raman-active functional groups. The methods utilize Raman spectroscopy to detect the presence or amount of water treatment polymer either directly or indirectly. The method provides the ability to detect or measure the amount of active water treatment polymer remaining in the sample.

14 Claims, 4 Drawing Sheets

COMPOSITIONS AND METHODS FOR THE DETECTION OF WATER TREATMENT POLYMERS

FIELD OF THE INVENTION

This relates generally to assays, and more particularly to compositions and assays for the detection of water treatment polymers.

BACKGROUND OF THE INVENTION

Water-soluble polymers are used in various aqueous systems, for example, as mineral dispersants, as water-treatment additives for boiler waters, cooling towers, reverse osmosis applications, sugar refining, paper production, geothermal processes and oil wells, and as detergent additives acting as builders, anti-filming agents, dispersants, sequestering agents and encrustation inhibitors. Water soluble polymers also play a role in coagulation and flocculation for waste water and drinking water clarification, and are also useful in mining, dewatering, and similar systems. In aqueous systems, it is often desirable to know the level of polymer in the system. However, the level of active polymer is not simply a function of how much polymer has been added. The polymer may have adhered to a surface, may have flocculated out of the water with sediment, or the polymer itself may have decomposed. Because polymers generally add cost to processes employing them, it is desirable to be able to use them efficiently.

Various homopolymers, copolymers, and terpolymers are used for water treatment. For example, polyacrylic acid-based polymers are used as water treatment polymers, such as for the treatment of industrial cooling water to prevent corrosion and mineral deposits, or scale. Phosphonic acid derivatives (HEDP, AMP) are also useful for the delivery of both scale and corrosion inhibition. In addition, metals such as molybdenum and various phosphates can be applied in conjunction with copolymers to deliver corrosion inhibition. Similarly, acrylamide copolymers are used.

Generally, active water treatment polymers remove dissolved minerals from cooling water by complexing with the minerals. Over time, the complexation sites of the water treatment polymer molecules become saturated. The polymer molecules then become "bound" or inactive and are unable to remove any additional minerals from the cooling water.

To prevent corrosion and scale damage to machinery, as the water treatment polymers are inactivated they must be removed and replaced by active polymers. Thus, active polymers must be continually fed into the cooling water to replace the inactive polymers. Maintaining the proper feed level for the active polymers is essential for optimum performance of the cooling water system. An improper feed rate can lead to serious problems. For example, an insufficient amount of active polymer can result in the water treatment being overwhelmed by dissolved minerals, thereby causing severe corrosion or scale deposit. On the other hand, maintaining too high a level of the active polymer is expensive and results in an inefficient method for treating industrial cooling water.

Although several methods are available for determining the concentration of polymer in an industrial cooling water system, these techniques are unsatisfactory because they only determine the concentration of total polymer, i.e., active plus inactive polymer, and do not provide information regarding the concentration of active polymer alone. Moreover, available methods suffer from a lack of specificity and/or sensitivity. For example, existing methods for detecting water treatment polymers, such as sulfonated copolymers of acrylic acid (sulfonated copolymers), involve the use of colloid titration with PVSK (poly-vinyl sulfate potassium), complexation with Hyamine 1622, or reaction of excess magnesium with chrome azurol S.

The above tests detect any polyanionic material and do not distinguish between active and inactive polymer concentrations. In addition, these methods have a detection threshold of only about 50 ppm polymer. Therefore, the total amount of active sulfonated polymer in an industrial cooling water system cannot currently be inexpensively, rapidly or reliably determined.

Furthermore, currently available methods collect a sample at a given point in time, thereby providing the operator with only a snap shot rather than a moving picture in a highly dynamic system that is seeing a tremendous amount of change caused by chemical and physical stresses to the treatment polymer.

Cationic polymers are used in several areas of industrial water treatment such as paper manufacture, effluent stream clarification, sludge dewatering, mineral process and others. When discharged into the environment, excessive amounts of cationic polymers may be problematic. It is therefore desirable to know, with specificity and precision, the amount of residual cationic polymer in a sample prior to discharge. Many currently available methods of determining cationic polymer concentrations in waste water and other water treatment systems suffer from a lack of specificity or sensitivity as with the sulfonated copolymer detection methods described above. Therefore, highly sensitive methods having specificity for particular water treatment polymers and methods having the ability to provide real time measurements of available, active polymer are needed.

BRIEF SUMMARY OF THE INVENTION

Compositions and methods for the detection of water treatment polymers using Raman spectroscopy are provided. Methods for measuring or quantifying the amount of water treatment polymer in a sample, such as an industrial, commercial, or municipal water sample, are also provided.

The compositions contain water treatment polymers that have been modified to include one or more Raman-active functional groups.

The methods utilize Raman spectroscopy to detect the presence or amount of water treatment polymer either directly or indirectly. The water treatment polymer to be detected can be either an active water treatment polymer or an inactive water treatment polymer.

In one embodiment, active water treatment polymer is bound to a Raman-active substance, such as a metallic mineral, and the complex is detected using a Raman spectrometer. In another embodiment, the water treatment polymer is modified in such a way that it is Raman-active and the modified water treatment polymer is detected by Raman spectrometry. In yet another embodiment, a Raman-active tracer molecule that binds to the water treatment polymer is added to a solution containing the water treatment polymer and changes in the concentration of bound and free tracer are detected.

DETAILED DESCRIPTION

Figure 1:
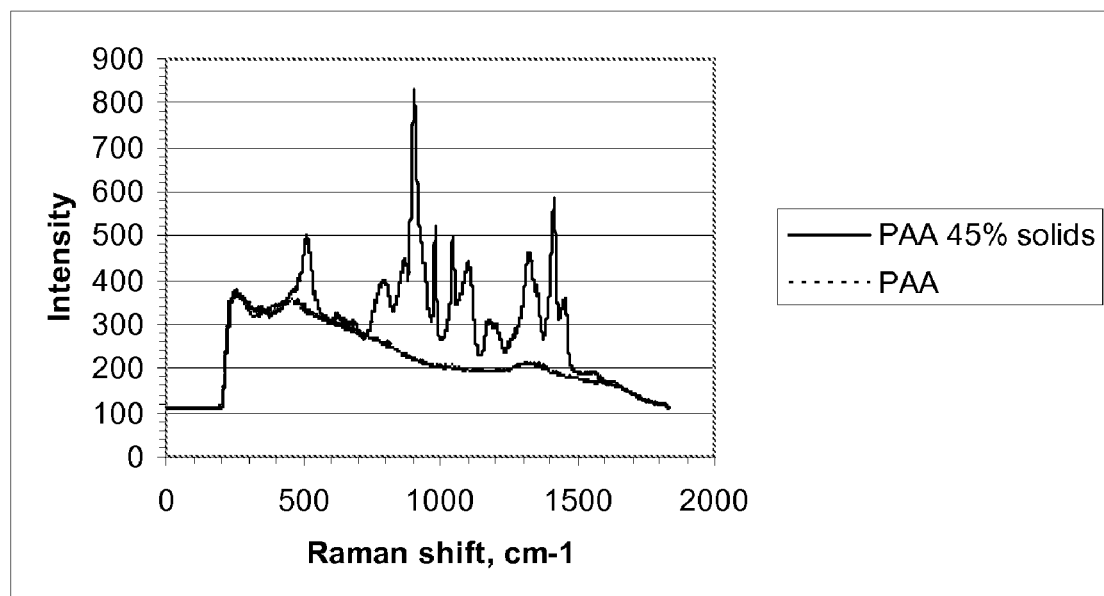
FIG. 1 is a graph of relative intensity versus Raman shift showing the Raman spectra of PAA as the concentrated stock product (45% solids) and at a typical working concentration of 15 ppm.

Compositions and methods for the detection of water treatment polymers using Raman spectroscopy are described herein. Also described are methods for measuring or quantifying the amount of water treatment polymer in a sample. The compositions are water treatment polymers that have been modified to include one or more Raman-active functional groups. The methods utilize Raman spectroscopy to detect the presence or amount of the water treatment polymer either directly or indirectly.

In one embodiment, active water treatment polymer is bound to a Raman-active substance, such as a metallic mineral, and the complex is detected using a Raman spectrometer. In another embodiment, the water treatment polymer is modified in such a way that it is Raman-active and the modified water treatment polymer is detected by Raman spectrometry. In yet another embodiment, a Raman-active tracer molecule that binds to the water treatment polymer is added to a solution containing the water treatment polymer and changes in the concentration of bound and free tracer are detected.

Raman Spectroscopy

When a molecule is irradiated, photons are elastically scattered. Generally, the scattered photons have the same energy (and accordingly, wavelength) as the incident photons. However, a small fraction of the photons are scattered at optical frequencies different from the frequency of the incident photons. Generally, these scattered photons are at an energy level that is less than the incident photons. Raman spectroscopy is a type of spectroscopy that measures this "Raman scattering". The scattered photons generally result from a molecule undergoing transitions in the vibrational, rotational or electronic state of a molecule. Of most interest in Raman spectroscopy are those transitions that are vibrational in nature.

Vibrational Raman scattering measures the difference in energy between the incident photon and the Raman scattered photon from these molecular vibrations. A Raman spectrum plots the intensity of scattered light versus the energy difference.

In other words, Raman spectroscopy uses the frequency of scattered light to identify molecules by a vibrational technique. Generally, individual molecules can be identified by characteristic vibrational modes that a particular molecular structure undergoes, which are dependent on the types of bonds present in that molecule.

One advantage that the Raman technique has over IR (infrared) spectroscopy, when looking at inorganic systems, is that Raman allows the use of aqueous solutions when investigating samples. In inorganic systems the metal-ligand bonds are generally in the region of from about 100 to 700 cm$^{-1}$, a region in IR spectroscopy that is experimentally difficult to study. In Raman, this region is not difficult to study. Raman studies of these inorganic aqueous solutions are of much use in gleaning useful information about the composition, structure, stability and coordination of the compounds in the composition.

Raman spectra are also often of more use then IR spectroscopic studies for organic compounds as the Raman spectra may yield more information than the corresponding IR study. For example, the double bond stretching frequency in Raman yields a stronger signal than in a corresponding IR study. The position (i.e., the frequency) of this stretching frequency is dependent upon the nature of the substituents that are present on or near the double bonds as well as their geometry on them.

Further advantages of Raman are the relatively small sample size needed to perform studies, the minimal sensitivity towards interfering water resonances, the good spectral detail (i.e., the spectral resolution is often superior to that seen in IR spectroscopy), the advantageous signal to noise considerations that are attained by the photomultiplier detectors used in Raman (relative to the thermal detectors used in IR), as well as the ability to give good information regarding the conformational and geometric environment. Moreover, because the spectral resolution in Raman is better than, for example, IR spectroscopy, quantitative measurements tend to be more facile as one does not have to deal with overlapping resonances. Generally, in a composition containing a mixture of components, the component amounts can be determined with precision to a less than 1% error rate (See Nicholson, *Anal Chem.* (1960), 32, 1634).

Raman spectroscopy is a generic form of spectroscopy that involves many variations. For example, the development of tunable lasers in the 1970s allowed Raman spectroscopy to be used for Resonance Raman Spectroscopy and for coherent Anti-Stokes Raman Spectroscopy. These tunable lasers allowed the enhancement of Raman lines by as much as a million fold by employing radiation that is close in frequency to the absorption peak of an analyte. Tunable lasers allowed the selection of wavelengths from the UV to the near IR region. Techniques such as sample flow have prevented sample heating (meaning the laser is focused on only a tiny fraction of a sample for a very short period as the sample is being moved through the excitation from the laser).

The sensitivity of Raman spectroscopy may be adversely affected by the competing phenomena of fluorescence emission spectroscopy. When the excitation photon is close in energy in these two types of spectroscopy, there is the possibility of interference. Interfering Stokes fluorescence can be mitigated by employing certain Raman techniques such as coherent Anti-Stokes Raman Spectroscopy. Coherent Anti-Stokes Raman Spectroscopy in one variation uses two tunable lasers, the first laser for sample excitation and pumping and the second laser for sample excitation. The second laser may be tuned (i.e., the frequency varied) until the difference between the two excitation frequencies is equal to the resonant frequency of a studied Raman line. At this point in time, coherence is generated and sample signal enhancement is seen.

Another variation of Raman is Surface Enhanced Raman Scattering spectroscopy (SERS). SERS gives enhanced signals of from approximately a thousand fold to a million fold due to the absorption of a compound to a metal surface (relative to the signal seen of the same compound in solution alone). Suitable metals for adsorption include gold, silver, and copper. Enhancement arises from at least two sources, 1) an enhanced electromagnetic field that is produced at the surface of the metal (generating an extended surface electronic state called a surface plasmon resonance), and 2) enhanced signal generated by the formation of a charge transfer complex (between the compound being observed and the metal surface). Transitions from the charge transfer complex may occur in the visible region of the electromagnetic spectrum, resulting in resonance enhancement.

The intensity generated from surface plasmon resonance is dependent on factors including but not limited to the morphology of the metal surface (e.g., how rough the surface is—the rougher the surface the better the enhancement), the wavelength of the incident light and other factors. By matching the incident light wavelength to a value close to the plasma wavelength of the metal employed on the surface, further enhanced values may be obtained.

Further enhancement can be achieved by employing or sampling certain types of molecules. For example, molecules with lone pairs of electrons or molecules with pi clouds show exceptionally strong SERS signals, such as nitrogen or oxygen containing rings (or aromatic rings with adjacent oxygen or amines) such as pyridines, pyrimidines, purines, imidizoles, oxazoles, pyrroles, oxiranes, aziridines, furans, phenols, anisoles, anilines, and other oxygen, nitrogen and other heteroatom-containing (e.g., sulfur, selenium, phosphorous, tellurium, arsenic, etc.) monocyclo- and polycyclo-rings.

In an embodiment, the Raman spectroscopy may undergo enhancement by employing radiation from a region of the electromagnetic spectrum that is close in frequency to the absorption peak of an the compound that is being tested (e.g., an analyte). In a variation of this embodiment, one or more tunable lasers may be used in the Raman spectroscopic method.

Moreover, many water treatment polymers are film formers. They are able to provide cathodic corrosion inhibition by creating a coating. Corrosion increases when this film is compromised by underdosing, or stressing the polymer (such as with chlorination). With this in mind, one can employ an online application in which one is continually looking at the amount of polymer bound to a fixed sampling area. If the sampling substrate both binds and releases the polymer like the general treated system, then this is a good proxy for dosage control. A surface on which this technique should be effective includes a carbon steel surface.

Water Treatment Polymers

The water treatment polymers to be detected or measured by the method described herein include those used in the treatment of aqueous systems to ameliorate or cure problems associated with particulates and mineral scale, corrosion, emulsification, flocculation and other contaminations. The monomers that make up these polymers may be anionic, cationic, non-ionic or zwitterionic.

Exemplary anionic monomers containing carboxylic and/or sulfonic functionalities include, but are not limited to, (meth)acrylic acids and alkali, alkaline earth or ammonium salts thereof, dicarboxylic acids such as maleic acid, fumaric acid and itaconic acid including the anhydrides and the alkali, alkaline earth or ammonium salts thereof. Other anionic monomers include the allyloxybenzenesulfonate monomers as described in U.S. Pat. No. 4,892,898, which is herein incorporated by reference in its entirety, (meth)allylsulfonate and the alkali, alkaline earth or ammonium salts thereof, and vinyl sulfonic acid and the alkali, alkaline earth or ammonium salts thereof, acrylamido alkyl or aryl sulfonates such as 2-acrylamido-2-methyl propane sulfonic acid.

Cationic monomers include quaternary ammonium functionalities such as diallyldimethyl ammonium chloride (DADMAC), (meth)acrylamidopropyltrimethyl ammonium chloride ((M)APTAC), quaternary aminomethyl(meth)acrylamide (QAMAM), methacryloxyethyltrimethyl ammonium chloride (METAC), acryloxyethyltrimethyl ammonium chloride (AETAC), acrylamidoethylpropyl trimethyl ammonium chloride (AMPTAC), diethyldiallyl ammonium chloride (DEDAAC) and trimethylallyloxyethyl ammonium chloride (TAAC). Non-ionic monomers include but are not limited to alkyl substituted or unsubstituted (meth)acrylamides, alkyl esters of (meth)acrylic acids, hydroxyalkyl esters of (meth) acrylic acids, and amino alkyl esters of (meth)acrylic acids. Zwitterionic monomers include but are not limited to monomers of unsaturated carboxyl, sulfoxyl or sulfate-substituted amines.

Preferred water treatment polymers to be detected or quantified, directly or indirectly, using the method described herein include, but are not limited to, sulfonated or carboxylated copolymer molecules having, as a backbone, acrylic acids and acrylamides and/or their corresponding esters, such as polyacrylic acid and sulfonated copolymers of acrylic acid.

Although water treatment polymers themselves are generally not detectable by Raman spectroscopy, the polymers may be modified in such a way that they include a chemical moiety that is detectable or the polymers can be combined with a tracer molecule that is detectable. Alternatively, water treatment polymers that complex to Raman-active substances in the aqueous environment to which they are added (such as contaminants in a water cooling tower) can be monitored indirectly by detecting the Raman-active substance to which they are bound. For example, many water treatment polymers are designed to bind minerals (such as metals). These minerals provide a resonant Raman frequency. Therefore, detection of increasing levels of signal at a predetermined Raman frequency provides an indication of the increasing concentration of inactive water treatment polymer in the sample (i.e., those polymers that are no longer able to prevent corrosion and/or scale). This provides valuable information regarding when it is advisable, necessary or required to add more water treatment polymer.

Modified Water Treatment Polymer

In accordance with the method described herein, Raman spectroscopy is employed to detect and determine the concentration of water treatment polymers in an aqueous sample directly and/or indirectly.

For an embodiment in which direct detection is employed, the water treatment polymer is modified or designed to contain one or more functional groups that are detectable by Raman spectroscopy. In one variation, the functional group on the water treatment polymer resonates at a given frequency without other overlapping resonances so that the modified water treatment polymer is accurately quantified. In another variation, the water treatment polymer is modified or designed to contain one or more functional groups that are detectable by Raman spectroscopy at a different frequency when in a non-complexed (active) and/or complexed (inactive) state. This allows the absolute amounts of total polymer, or alternatively, the relative amounts of active and/or inactive water treatment polymer to be calculated. The total amount of polymer can be calculated by using different levels of the active and inactive states and making a calibration curve. The relative amounts of the active and inactive states can then be ascertained by comparing the measured value to the calibration curve (see for example, *European Journal of Mineralogy*; June 2006; v. 18; no. 3; p. 331-335).

Due to the high resolution and sensitivity of Raman frequencies to different chemical environments (as described above), Raman spectroscopy is a useful technique for deducing aggregated water treatment polymers. In this embodiment, these alternative frequencies can be measured that allow one to deduce when water treatment polymers are in an aggregated state versus in a non-aggregated state.

As an example, the Raman-active polymer may exhibit different spectra when either bound (unavailable) or free (available) to, for example, calcium carbonate. One need only monitor a unique frequency for each (or either) state to calculate the amount free, bound and total (total=free+bound).

Raman-active Tracer

In an alternative embodiment of the present method, a water treatment polymer is indirectly detected by adding a tracer to the solution containing the water treatment polymer to be detected or quantified and then detecting the tracer by Raman spectroscopy. It will be understood by those skilled in the art that both direct and indirect detection can be used simultaneously. In other words, both a modified water treatment polymer, as described above, and a tracer, as described below, can be employed in the method provided herein.

The tracer is an organic or inorganic compound capable of detection by Raman spectroscopy. For example, the tracer can be any of the compounds listed as tracers in, for example, U.S. Pat. Nos. 6,040,406; 5,736,405; 5,654,198; 5,416,323; 5,389,548; 5,304,800, and 5,266,493, or in Lin-Vien, D., Colthup, N., Fateley, W., & Grasselli, J. (1991) THE HANDBOOK OF INFRARED AND RAMAN CHARACTERISTIC FREQUENCIES OF ORGANIC MOLECULES (Academic Press, San Diego, Calif.), which are incorporated by reference herein.

In one variation of this embodiment, a predetermined concentration of a Raman-active tracer is added, with the water treatment polymer, to the environment in which the water treatment polymer is being used. The tracer binds to all water treatment polymer present in the environment or sample. The concentration of tracer is monitored by Raman spectroscopy, and the concentration of tracer is directly related to the concentration of water treatment polymer concentration. For example, the tracer can be an inorganic metal-containing compound that binds to the water treatment polymer, and the tracer resonates in a Raman spectra at one frequency when the tracer is bound to the water treatment polymer and at a different frequency when the tracer is not bound to the polymer. The relative amounts of tracer are then calculated by monitoring the respective Raman resonant frequencies to provide the total amount of water treatment polymer in a sample.

In a variation, a fixed amount of tracer is used and is added to the polymer to calculate total polymer. It should be noted that the tracer does not need to bind to the polymer. In this embodiment where the tracer does not need to bind to the polymer, if one knows and adds the tracer at a fixed dosage relative to the "neat" polymer, then one can use the tracer concentration only as a proxy for how much polymer was added, or alternatively, the dosage of the chemical added. One need not know if the active ingredient is available or not, but need only know how one dosed at the defined amount. Alternatively, one can calculate the amount of free and bound tracer by using a tracer that has different resonance frequencies depending whether its free or bound to the polymer. The total amount of polymer can be calculated by summation. In either of these cases, it should be recognized that one can calculate the total polymer.

Alternatively, the tracer can be used to quantitate the relative amounts of active and/or inactive water treatment polymer. For example, a tracer is chosen that does not bind to the water treatment polymer if the water treatment polymer is inactive (bound, complexed or associated with particulates that cause the aforementioned corrosion or scale problems). The tracer resonates in a Raman spectra at one frequency when the tracer is bound to the water treatment polymer and at a different frequency when the tracer is not bound to the polymer. Relative amounts of tracer are then determined by monitoring the appropriate Raman resonant frequencies, and the concentration of active water treatment polymer in a sample is calculated. Similarly, a tracer is chosen that does not bind to active water treatment polymer. The relative amounts of tracer are then determined by monitoring the appropriate Raman resonant frequencies and the concentration of inactive water treatment polymer in a sample is calculated.

In a variation, one can employ a tracer that is indicative of the initial dosage. In this variation, the tracer does not bind to anything, but is blended into the product at a fixed ratio and thus is indicative of total product added. One can employ another tracer that binds an "active" chemical or is only available when the "active" chemical is available. By testing for the amount of this other tracer, one can deduce the rate and degree of degradation of polymer. Alternatively and/or additionally, it can be used to adjust the dosage of other additives.

In a further variation, relative concentrations of both active and inactive water treatment polymers in a sample are determined using one or more tracers. For example, one tracer is added the binds to both active and inactive water treatment polymer, but is detected by Raman spectroscopy at one wavelength when bound to active polymer and detected at a different wavelength when bound to inactive polymer. Alternative two tracers are added; one bind to active water treatment polymer and is detected by Raman spectroscopy at a first wavelength and the other binds to inactive water treatment polymer and is detected by Raman spectroscopy at a second wavelength. In this way, one can calculate the concentration of active water treatment polymers that are available to prevent corrosion and/or scale versus the water treatment polymers that are inactive and no longer available to prevent corrosion and/or scale.

As explained above, sulfonated or carboxylated copolymer molecules that have as a backbone acrylic acids and acrylamides and/or their corresponding esters are useful as water treatment polymers to reduce corrosion and/or scale in industrial cooling waters. Thus, as a specific example of a variation of the present method, a tracer such as phthalocyanins and other polycyclic and heterocyclic aromatic compounds that bind these sulfonated or carboxylated copolymer molecules is added to the stock solution of water treatment polymer. Tracer that is bound to the water treatment polymer and/or tracer not bound to the water treatment polymer or polymers are monitored by Raman spectroscopy. In this way, the concentration of water treatment polymer in a sample can be determined. The tracer bound to water treatment polymer bound will show a characteristic Raman peak at a predetermined frequency and the tracer free in solution, or unbound to the water treatment polymer, will have no peak or will show a characteristic peak at a different frequency. By measuring the relative amounts of signal at each frequency, one can calculate the relative amounts of tracer and thereby calculate the concentration of water treatment polymer in the sample.

The detection of Raman-active substances bound to water treatment polymers, water treatment polymers modified to include a Raman-active molecule and Raman-active tracers, as described above, are useful for controlling and managing effective concentrations of water treatment polymer in industrial, commercial, or municipal water systems. If the detected concentration of water treatment polymers is found to be too low, additional water treatment polymers can be added to treat the water. Alternatively, if the concentration of water treatment polymers is found to be too high, measures can be taken to reduce or maintain the levels such as by diluting the water treatment polymer with additional water to be treated or by refraining from the addition of further water treatment polymer until the relative concentration decreases.

Detection Methods

Because Raman is a relatively sensitive technique that allows for fast detection times (as well as signal averaging, which further increases sensitivity), Raman can be used as a "real time" technique that allows for quickly assessing relative concentrations of sampled chemical species. Accordingly, the detection of Raman-active tracers, modified water treatment polymer or water treatment polymer bound to Raman-active moiety can be observed in a sample, on-line, in situ, in-line, real-time, by continuous monitoring or by any combination thereof. It is contemplated, and therefore within the scope of the present method, that a discreet self-contained sample can be removed from an industrial water sample and placed into a Raman spectrometer. For example, a tap may be turned on to acquire a small sample. The sample can then be subjected to analysis in a Raman spectrometer (either a portable spectrometer or a non-portable spectrometer). Alternatively, rather than removing a sample from the water treatment system, the detector is situated in-line or in situ so that it is focused through a window or opening such that the focal point of the laser is in the sample, or is interrogating the sample as it flows past the focal point of the laser, within the water treatment system being monitored.

In an embodiment of the invention, any of the above described plurality of Raman associated techniques can be used to monitor and/or measure chemical species. The detection of Raman-active tracers or Raman-active water treatment polymer include the methods such as Raman Scattering, Surface Enhanced Raman Scattering, Resonance Raman Spectroscopy, or coherent Anti-Stokes Raman Spectroscopy, alone or in combination.

Moreover, because Raman is sensitive to differences in chemical environment, it can be used to measure any of a plurality of chemical properties. Accordingly, in an embodiment, the present method uses Raman for the simultaneous measurement of multiple parameters within a water sample such as pH, temperature, water treatment polymer concentration, water treatment polymer availability, ion concentration, tracer concentrations, turbidity, dispersion, and other chemical properties.

In an alternative embodiment, the present method relates to an on-line monitor for the determination of a water treatment polymer in a water system using Raman spectroscopy to measure the concentration of a Raman-active water treatment polymer or a Raman-active tracer molecule added to the water treatment polymer product at a concentration relative to the water treatment polymer that is known.

Raman spectroscopy can also be combined with one or more other spectroscopic techniques (or excitation energies in the various regions of the electromagnetic spectrum that those spectroscopic techniques use) to deduce information about concentrations, relative amounts, chemical species identification and other chemical parameters. In a variation of the embodiment, the present method relates to the use of multiple spectrophotometric techniques simultaneously such as infrared, near infrared, Raman, fluorescence, or UV/V is to determine the concentration or availability of water treatment polymer using Raman-active tracers or Raman-active water treatment polymer. In a variation of this embodiment, absorption spectroscopic techniques can be used to enhance Raman resonant frequencies and to provide greater sensitivity.

Therefore, the present method provides a method of detecting a water treatment polymer using Raman spectroscopy. In a variation of this method, the method involves ascertaining a concentration of the water treatment polymer. Concentrations of active polymer, inactive polymer, or both can be determined. In a further variation of the embodiment, the water treatment polymer is detected during its use as a corrosion and/or scale inhibitor.

The method described herein may include additional steps such as adding additional active water treatment polymer to industrial water during its use as a corrosion and/or scale inhibitor if the concentration of active water treatment polymer is less than the concentration of inactive water treatment polymer. Alternatively, if the concentration of the active water treatment polymer falls below a certain threshold value, additional amounts of active polymer may be added to the industrial water that is being treated. In accordance with the method, one or more samples of industrial water to be tested can be obtain simultaneously, sequential or continuously.

In one embodiment, the relative or absolute concentration may be ascertained by measuring a peak intensity from a Raman vibrational mode frequency of an organic or inorganic species. An exemplary Raman vibrational mode frequency is between about −300 and 4400 $cm^{-1}$. In a preferred embodiment, the spectra of a polymer to be detected in the sample is determined and then a Raman active molecule is chosen that has a peak intensity at a wave number where the spectra of the polymer exhibits a low vibrational mode frequency or where the vibrational mode frequency of the polymer is absent. In this way, interference with the vibrational mode frequency of the polymer can be minimized or avoided so that more highly sensitive or selective detection results are obtained.

The method may ascertain relative concentrations or other physical data by Raman spectroscopy alone, or in connection with other spectroscopic methods. Any of a plurality of spectroscopic methods can be used including but not limited to one or more of infrared, near infrared, Raman, fluorescence, and UV/V is spectroscopy.

The compositions and methods described herein will be further understood with reference to the following non-limiting example.

EXAMPLE 1

Detection of a Water Treatment Polymer and Quantitation of a Raman-active Tracer in a Solution of Water Treatment Polymer Using Raman Spectroscopy Materials and Methods.

Polyacrylic acid (PAA) (Colloid 207, 45% solids, MW 4500) was a gift from Kemira U.S.A. (Kennesaw, Ga.). 2-Mercapto-5-nitrobenzimidazole (2-MNB) and methanol were purchased from Aldrich (Milwaukee, Wis.). Raman spectra were obtained using a Kaiser Holospec™ instrument equipped with 532 nm and 785 nm diode lasers. The typical power at the sample was in the range of 10-100 $mW/cm^2$.

A solution of 15 ppm PAA was made in water (Milli Q). A 1% (w/v) stock solution of 2-MNB was made in methanol. The polymer solution was fortified to 0.1% 2-MNB. Serial dilutions of the 2-MNB-fortified polymer solution were made resulting in final polymer concentrations of 15, 7.5, 3.75, 1.875, 0.937 ppm polymer. Raman spectra were recorded for each of these various samples.

The results can best be seen in relation to the figures as follows:

FIG. 1 shows a Raman spectra (785 nm diode laser excitation) of PAA as the concentrated stock product (45% solids) and at a typical working concentration of 15 ppm. A characteristic Raman spectrum was obtained for the concentrated stock material but was not apparent at a typical working concentration of 15 ppm (0.0015%). In this case, use of more sensitive Raman techniques such as surface-enhanced Raman spectroscopy (SERS) may improve the detection of the dilute polymer. Alternatively, novel polymers can be constructed that incorporate specific chemical moieties capable of exhibiting resonance enhancement and the use of resonance-enhanced Raman spectroscopy. This will achieve greater sensitivity.

Figure 2:
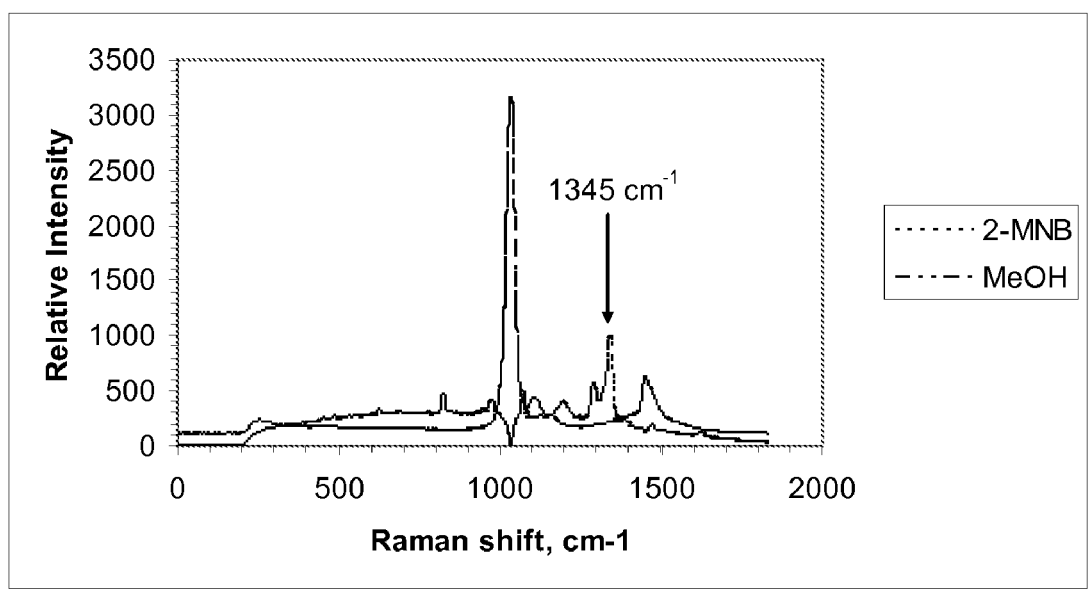
FIG. 2 is a graph of relative intensity versus Raman shift showing the Raman spectra of an example tracer molecule 2-MNB (1% (w/v)) that may be used to indicate the presence of polymer.
Figure 3:
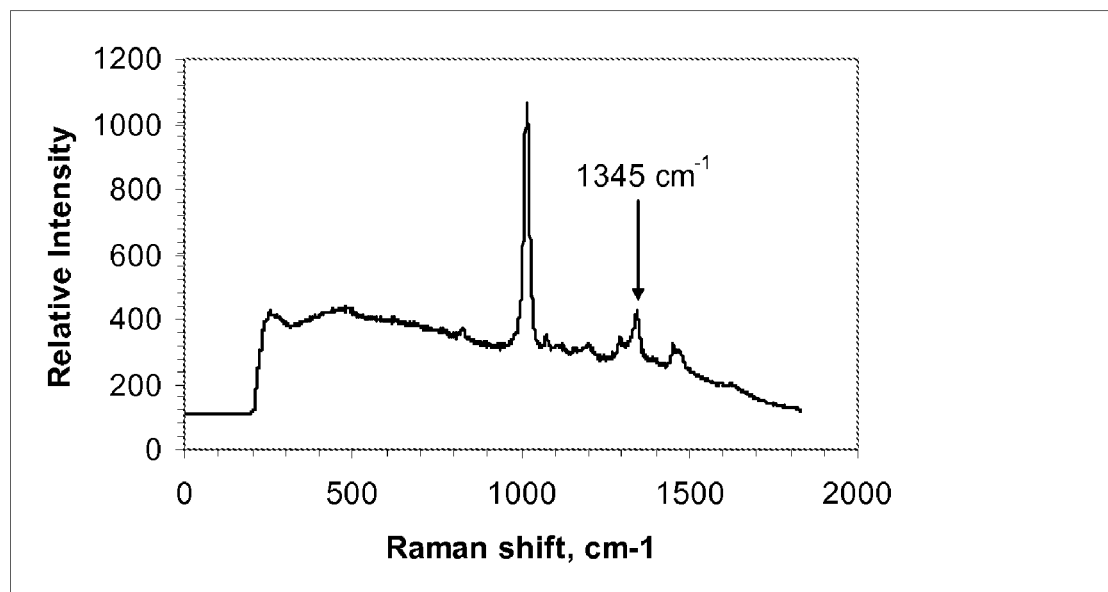
FIG. 3 is a graph of relative intensity versus Raman shift showing a prominent 2-MNB peak at 1345 cm$^{-1}$ when spiked into 15 ppm polymer.
Figure 4:
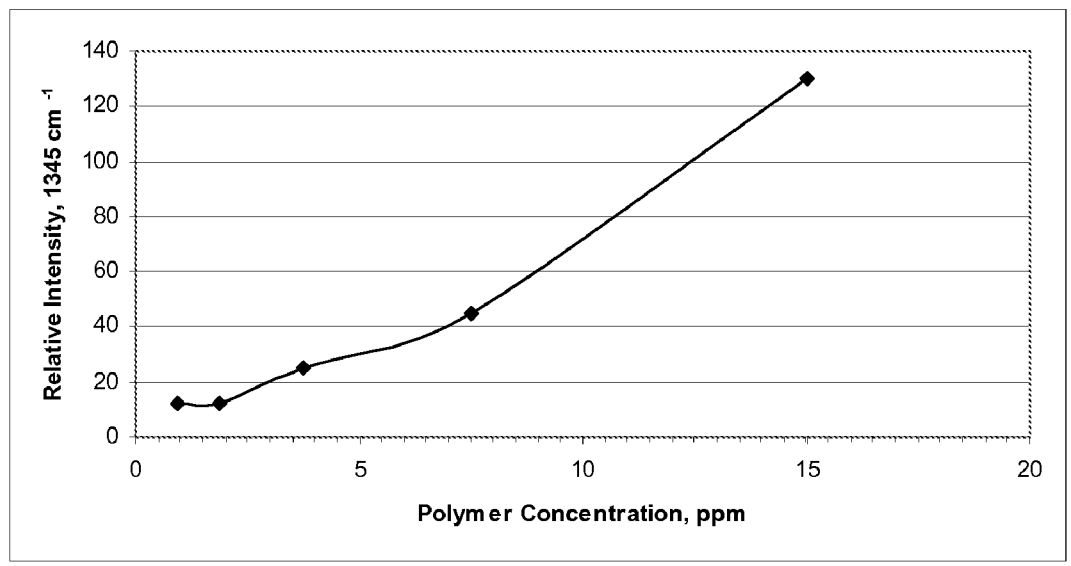
FIG. 4 is a graph of relative intensity of the prominent 2-MNB peak at 1345 cm$^{-1}$ as an indicator of polymer concentration in a useful working range.

FIG. 2 shows the Raman spectra of an example tracer molecule 2-MNB (1% (w/v)) that may be used to indicate the presence of the polymer, and methanol (100% (v/v)), the solvent used in formulating the stock tracer. The Raman-active tracer 2-MNB gave a characteristic Raman peak at 1345 cm$^{-1}$. Pure methanol gave a peak at 1034 cm$^{-1}$. When spiked into 15 ppm polymer, the 2-MNB peak at 1345 cm$^{-1}$ was prominent (see FIG. 3). This characteristic Raman peak at 1345 cm$^{-1}$ was used as an indicator of polymer concentration in a useful working range (see FIG. 4).

All scientific articles, publications, abstracts, patents and patent applications mentioned above are hereby incorporated by reference in their entirety.

While this composition and method has been described in specific detail with reference to the disclosed embodiments, it will be understood that many variations and modifications may be effected within the spirit and scope of the invention. It should be understood that any one or more element that is disclosed above can be combined with any other one or more element. When ranges are given, it is contemplated and therefore within the scope of the present invention that any real number value that fits within that given range is a contemplated endpoint for a subrange within that range, even if that real number value is not explicitly mentioned. Minor modifications that are known to those of skill in the art regarding Raman spectroscopy are also contemplated and therefore within the scope of the present invention. Further, the present invention is not to be limited by the above embodiments but rather is to be defined by the below claims.

We claim:

1. A method of detecting a water treatment polymer in an aqueous sample comprising subjecting the sample to Raman spectroscopy and detecting a signal at a predetermined frequency, wherein detection of the signal indicates the presence of the water treatment polymer in the sample.

2. The method of claim 1, wherein the water treatment polymer is bound to a Raman-active molecule that generates the signal.

3. The method of claim 1, wherein the water treatment polymer is a modified water treatment polymer containing one or more functionalities that are detectable by Raman spectroscopy.

4. The method of claim 1, wherein the water treatment polymer is combined with a Raman-active tracer.

5. The method of claim 1, wherein the signal is quantified and the quantity of signal provides a concentration of the water treatment polymer.

6. The method of claim 1, wherein the signal is generated by one or more members selected from the group consisting of Surface Enhanced Raman Scattering spectroscopy, Raman Scattering spectroscopy, coherent Anti-Stokes Raman Spectroscopy, and Resonance Raman Spectroscopy.

7. The method of claim 1, wherein the water treatment polymer detected is an active or inactive water treatment polymer.

8. The method of claim 1, wherein the sample is an industrial water sample.

9. The method of claim 1, wherein the signal measures a vibrational mode frequency of an inorganic species.

10. The method of claim 1, wherein the signal is produced by a Raman-active molecule has a peak intensity vibrational mode frequency that is low or absent in the vibrational mode frequency spectra of the water treatment polymer.

11. The method of claim 1, wherein the Raman spectroscopy is enhanced by employing radiation from a region of the electromagnetic spectrum close in frequency to the frequency of the signal.

12. The method of claim 1, wherein the signal is detected after excitation of the sample by one or more tunable lasers.

13. The method of claim 1 wherein the sample is an industrial, commercial, or municipal water system sample.

14. A modified water treatment polymer, wherein the water treatment polymer has been chemically modified to include a Raman-active functional group.

* * * * *